United States Patent [19]

Bianco

[11] Patent Number: 4,738,271
[45] Date of Patent: Apr. 19, 1988

[54] DEVICE FOR STORING, DISPENSING AND KEEPING IN A TAUT CONDITION AN INTERDENTAL FLOSS

[75] Inventor: Angelo Bianco, Turin, Italy
[73] Assignee: Lady Finanziaria S.r.l., Turin, Italy
[21] Appl. No.: 918,222
[22] Filed: Oct. 14, 1986

[30] Foreign Application Priority Data

Feb. 19, 1986 [IT] Italy ............................. 35586/86[U]

[51] Int. Cl.⁴ ............................................. A61C 15/00
[52] U.S. Cl. ...................................... 132/92 R; 132/91
[58] Field of Search ....................... 132/92 R, 92 A, 91

[56] References Cited

U.S. PATENT DOCUMENTS

| | | | |
|---|---|---|---|
| 1,990,404 | 2/1935 | Doner | 132/92 R |
| 2,577,597 | 12/1951 | Wright et al. | 132/92 R |
| 3,672,377 | 6/1972 | Greenacre | 132/92 R |
| 3,814,114 | 6/1974 | Roberts | 132/92 A |
| 3,871,393 | 3/1975 | Wharton | 132/92 A |
| 3,903,907 | 9/1975 | Knaus | 132/92 R |
| 3,915,178 | 10/1975 | Zellers | 132/92 R |

*Primary Examiner*—John J. Wilson
*Attorney, Agent, or Firm*—Sughrue, Mion, Zinn, Macpeak, and Seas

[57] ABSTRACT

A device for storing, dispensing and keeping in a taut condition an interdental floss comprises a hollow handle within which is housed a support member on which the interdental floss is wound. A fork extends from this handle and forms a structure for stretching the floss so as to form an active extended portion of floss usable for interdental cleaning. A clamp enables the extended floss on the fork to be tensioned and clamped.

2 Claims, 1 Drawing Sheet

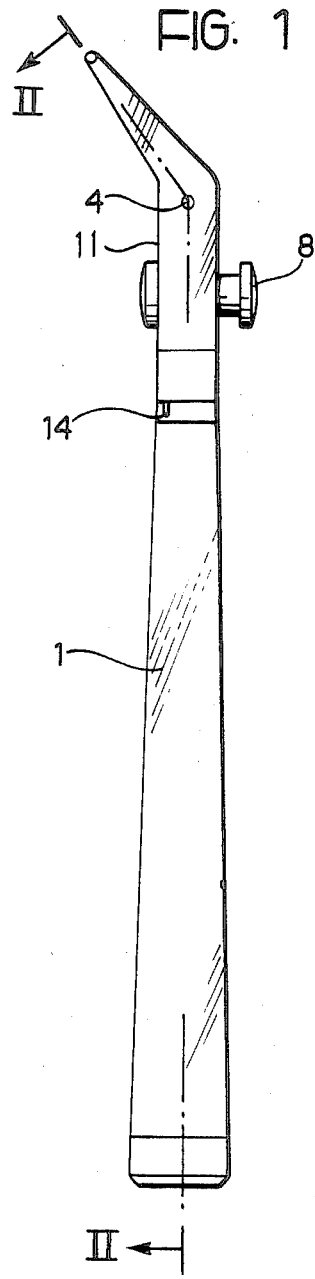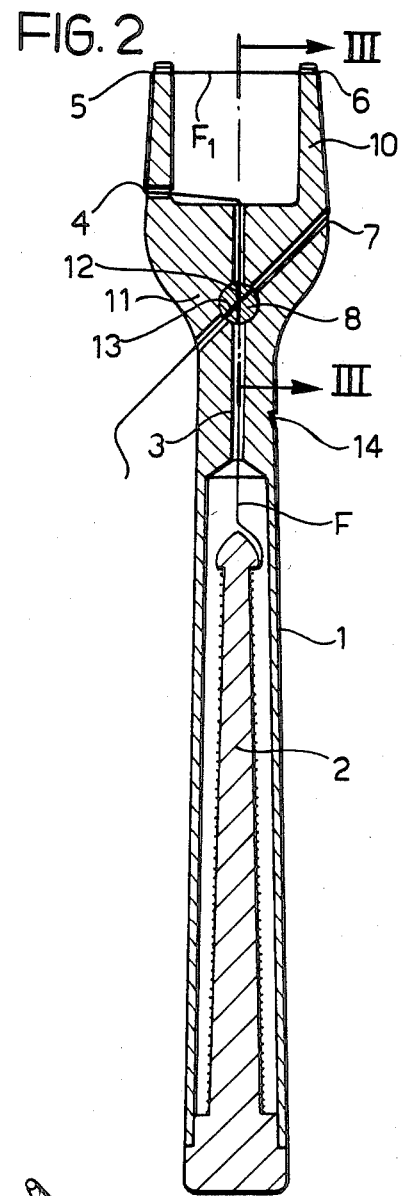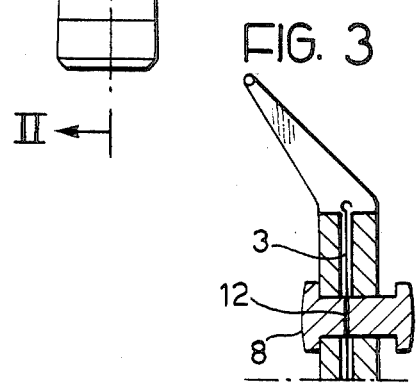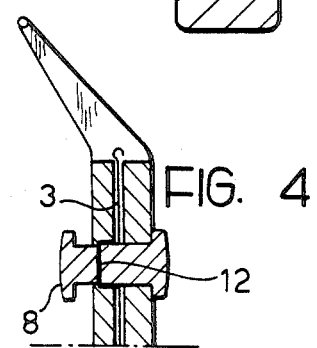

DEVICE FOR STORING, DISPENSING AND KEEPING IN A TAUT CONDITION AN INTERDENTAL FLOSS

BACKGROUND OF THE INVENTION

Particularly in recent years, the cleaning of teeth has assumed greater and greater importance. This cleaning is carried out in a through manner with the use of devices such as toothbrushes and dentifrice and, for interdental cleaning, a floss which enables food residue deposited in the interdental spaces to be removed.

The interdental floss used for this operation has been on the market for a number of years and is currently sold in packages from which it projects through a small hole. The user, in order to use the floss, must remove it from the package, cut a suffifcient length to enable it to be handled and held taut between the fingers and then pass it between one tooth and the next.

This operation is inconvenient to carry out, however, and involves a certain loss of time, as well as wastage of floss, in that the quantity of floss needed to enable it to be kept taut between the fingers is greater than that which would otherwise be needed for passage between the teeth.

SUMMARY OF THE INVENTION

The subject of the present invention is a device for storing, dispensing and tensioning the interdental floss in an optimum manner in order to reduce the wastage to a minimum and optimise the time needed for its use.

The device of the present invention is constituted by a hollow handle adapted to be gripped easily, which is tapered at one end and terminates at the tapered end in a fork which is shaped and angled relative to the handle.

Within the handle is a support member which is usually slightly conical and around which is wound a sufficient quantity of interdental floss for numerous operations of use.

The floss present within the handle and wound around the conical support member is unwound onto the two prongs constituting the fork by being passed through guide apertures provided in the device, so as to form a loop with a portion of floss tensioned between the free ends of the prongs of the fork.

At the base of the fork there is provided a floss clamp constituted by a member (preferably made of plastics as is also the entire device) which has a double-T-shaped longitudinal section and has two coplanar through-holes, the first aligned with a first guide through which the floss is made to project from the handle towards the fork and the second, which is generally inclined to the first, aligned with a return guide through which passes the free end of the floss tensioned on the fork.

The clamp has a greater width than the part of the device in which it is inserted so that it can undergo a transitional movement in a sense perpendicular to the plane of the two apertures. By acting on the clamp, that is, by sliding it relative to the body of the device, it is possible to offset the portions of floss which are located in the clamp relative to those present in the adjacent guide portions formed in the body of the device, with the consequent clamping of the floss. If the clamp is rotated, however, the floss is subjected to traction until the optimum tension in the portion extending between the two prongs of the fork is achieved.

The operation of the device is simple enough in that, to renew the portion of floss extending between the two prongs of the fork, that is, the portion which is passed into the interdental spaces, it suffices to disengage the clamp from the floss, slide out the necessary quantity of floss, and tension and clamp the floss again with the clamp. The part of the floss which has already been used may then be removed by cutting with a floss-cutting member disposed to one side of the handle of the device.

BRIEF DESCRIPTION OF THE DRAWINGS

What has been said briefly up to now will be better understood from the detailed description which follows, by way of example, with reference to the appended drawings, in which:

FIG. 1 is a side elevational view of the device of the invention,

FIG. 2 is a section taken on the line II—II of FIG. 1, and

FIGS. 3 and 4 are two sections taken on the line III—III of FIG. 2 with the floss clamp of the device illustrated in two different operating conditions.

DETAILED DESCRIPTION OF THE INVENTION

With reference to the drawings, the device of the present invention is constituted by a hollow handle 1 within which is housed a slightly conical member 2 around which an interdental floss F is wound. Preferably, the member 2 is constituted by an insert which is introduced into the cavity of the handle after the floss F has been wound onto it.

A fork 10 extends from the end of the handle 1 opposite that in which the member 2 is inserted, through a flat part 11 at the centre of which is located a clamp 8. The fork 10 and the handle 1 are preferably inclined to each other so as to make the device particularly easy to use.

The fork 10 has a solid structure and is traversed by holes or grooves 3, 4, 5, 6 and 7 which act as guides for the floss which is unwound from the member 2.

The path of the floss F is as follows. From the storing and dispensing member 2, the floss F is inserted in the guide 3 which extends axially from the cavity of the handle 1 towards the fork 2, passing right through and also traversing the clamp 8, the structure of which will be described more fully below. Once it has reached the base of the fork 10, the floss F is inserted in the hole 4 provided in one of the prongs and then made to project outwardly of the fork 10. The floss is then passed through the hole 5 provided at the free end of the prong in which the hole 4 is located and extends towards the hole 6 located at the free end of the other prong. From the hole 6, the floss F passes over the outer side of the fork and is re-introduced into the guide 7 which extends through the clamp 8.

Thus, a loop of floss F is formed the portion $F_1$ of which extends between the free ends of the prongs of the fork 10 (the holes 5 and 6) and this is used for interdental cleaning.

The clamp 8 is constituted essentially by a circular-sectioned pin which is slidably inserted in a corresponding hole formed in the flat part 11. The clamp 8 has a double-T-shaped longitudinal profile and has two through-holes 12, 13 for the floss F aligned with the guide 3 and the guide 7, respectively. As may be best seen in FIGS. 3 and 4, the axial extent of the body of the clamp 8 is greater than the thickness of the flat part 11 in which the clamp 8 itself is inserted. The clamp 8 may thus be moved along its longitudinal axis so as to offset the holes 12 and 13 provided therein relative to the guides 3 and 7. More precisely, the clamp 8 has the function of a floss clamp when the two holes 12, 13 are not coaxial with the guides 3 and 7 in the device (FIG. 4). However, when the holes 12, 13 are coaxial with the guide 3 and the guide 7 respectively (FIG. 3), the floss can slide freely within the guides 3, 4, 5, 6 and 7 to enable the portion $F_1$ used for cleaning to be renewed.

The floss clamp 8 also has another function, which is that of tensioning the floss F prior to clamping. In fact, because of the presence of the holes 12, 13, it suffices to rotate it in one sense or the other to tension the floss F before it is clamped. Thus, the user will have extremely quickly a floss which is always well tensioned, and the worn portion $F_1$ can be renewed rapidly without any wastage.

The device of the present invention also has a suitable floss cutter 14 (a blade or the like) attached to the handle 1 by means of which it is possible to cut the portion of the floss resulting from each operation to renew the floss used for interdental cleaning.

Variations may be made by an expert in the art to what has been described and illustrated, without thereby departing from the scope of the invention as in the following claims.

What is claimed is:

1. A dental floss applicator for storing, dispensing and maintaining in a taut condition an interdental floss, comprising:
   (a) a handle having an axially extending bore therein;
   (b) a conical member adapted to have a supply of dental floss thereon secured within said handle;
   (c) a flat portion contiguous with said handle and extending in the axial direction of said bore, said flat portion having a first hole extending axially through said flat portion from the bore in said handle to an end of said flat portion remote from said handle, said flat portion having a second hole extending from one side of said flat portion to the opposite side of said flat portion and intersecting the first hole;
   (d) a fork arrangement contiguous with said flat portion and extending at an angle therefrom, said fork arrangement having first and second spaced prongs, said first prong having a third hole in a base portion thereof and a fourth hole in a tip portion thereof, and said second prong having a fifth hole in a tip portion thereof; and
   (e) clamp means disposed in a through-hole in said flat portion at the intersecting of the first and second holes for maintaining the floss in a taut condition between said prongs when the dental floss extends from the bore in said handle through said first, third, fourth, fifth and second holes in sequence and is engaged by said clamp means whereby the portion of the floss between the fourth and fifth holes is used for interdental cleaning,; wherein said clamp means comprises a clamp having a central portion slidably and rotatably inserted in said through-hole and an enlarged end portion at each end to limit sliding and prevent removal of the clamp and having first and second clamping apertures in a central portion which are coaxial with the first and second holes, respectively in said flat portion in a first position of said clamp, said clamp being rotatable within said through-hole to tension the floss and said clamp being axially slidable in said through-hole between said first position and a second position wherein said first and second clamping apertures are misaligned with said first and second holes respectively in said flat portion to frictionally engage the dental floss between a periphery of the central portion of said clamp and an interior surface of said through-hole and hold the floss under tension.

2. Device according to claim 1, further comprising floss-cutting means disposed on said flat portion for cutting an expandable portion of the floss.

* * * * *